US00PP27796P3

(12) United States Plant Patent
Pieters

(10) Patent No.: US PP27,796 P3
(45) Date of Patent: Mar. 21, 2017

(54) ***CHRYSANTHEMUM* PLANT NAMED 'AKILON GOLD'**

(50) Latin Name: *Chrysanthemum×morifolium*
Varietal Denomination: Akilon Gold

(71) Applicant: Dirk Pieters, Oostnieuwkerke (BE)

(72) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 22 days.

(21) Appl. No.: 14/545,961

(22) Filed: Jul. 10, 2015

(65) Prior Publication Data

US 2017/0013760 P1 Jan. 12, 2017

(51) Int. Cl.
*A01H 5/02* (2006.01)

(52) U.S. Cl.
USPC ..... Plt./289

(58) Field of Classification Search
USPC ..... Plt./289
See application file for complete search history.

*Primary Examiner* — Anne Grunberg
(74) *Attorney, Agent, or Firm* — C. A. Whealy

(57) ABSTRACT

A new and distinct cultivar of *Chrysanthemum* plant named 'Akilon Gold', characterized by its upright, outwardly spreading and uniformly rounded plant habit; short internodes and freely branching habit; dense and full plant habit; medium green-colored leaves; uniform and freely flowering habit; and decorative-type inflorescences that are golden yellow in color.

1 Drawing Sheet

Botanical designation: *Chrysanthemum×morifolium.*
Cultivar denomination: 'AKILON GOLD'.

BACKGROUND OF THE INVENTION

The present invention relates to a new and distinct cultivar of *Chrysanthemum* plant, botanically known as *Chrysanthemum×morifolium* and hereinafter referred to by the name 'Akilon Gold'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant is a naturally-occurring whole plant mutation of *Chrysanthemum×morifolium* 'Akilon Pink', not patented. The new *Chrysanthemum* plant was discovered and selected by the Inventor as a single flowering plant from within a population of plants of 'Akilon Pink' in a controlled greenhouse environment in Oostnieuwkerke, Belgium in September, 2012.

Asexual reproduction of the new *Chrysanthemum* plant by vegetative terminal cuttings was first conducted in a controlled greenhouse environment in Oostnieuwkerke, Belgium in January, 2013. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Akilon Gold'. These characteristics in combination distinguish 'Akilon Gold' as a new and distinct *Chrysanthemum* plant:

1. Upright, outwardly spreading and uniformly rounded plant habit.
2. Short internodes and freely branching habit; dense and full plant habit.
3. Medium green-colored leaves.
4. Uniform and freely flowering habit.
5. Decorative-type inflorescences that are golden yellow in color.

Plants of the new *Chrysanthemum* differ primarily from the parent, 'Akilon Pink', in ray floret color as plants of new *Chrysanthemum* have golden yellow-colored ray florets and plants of 'Akilon Pink' have soft pink-colored ray florets.

Plants of the new *Chrysanthemum* can be compared to plants of *Chrysanthemum×morifolium* 'Viviana Yellow', disclosed in U.S. Plant Pat. No. 21,898. In side-by-side comparisons conducted in Oostnieuwkerke, Belgium, plants of the new *Chrysanthemum* differed from plants of 'Viviana Yellow' in the following characteristics:

1. Plants of the new *Chrysanthemum* were denser and fuller than plants of 'Viviana Yellow' as plants of the new *Chrysanthemum* were more freely branching and had shorter internodes than plants of 'Viviana Yellow'.
2. Leaves of plants of the new *Chrysanthemum* were smaller and lighter green in color than leaves of plants of 'Viviana Yellow'.
3. Ray florets of plants of the new *Chrysanthemum* were golden yellow in color whereas ray florets of plants of 'Viviana Yellow' were yellow in color.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Akilon Gold' grown in a container.

DETAILED BOTANICAL DESCRIPTION

The aforementioned photograph and following observations and measurements describe plants grown in 19-cm containers in an outdoor nursery in Oostnieuwkerke, Belgium during the spring and summer and under cultural practices generally used in commercial *Chrysanthemum* production. During the production of the plants, day temperatures ranged from 18° C. to 21° C. and night temperatures ranged from 10° C. to 15° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Akilon Gold'.

Parentage: Naturally-occurring whole plant mutation of *Chrysanthemum×morifolium* 'Akilon Pink', not patented.

Propagation:

*Type*.—Vegetative terminal cuttings.

*Time to initiate roots, summer*.—About 14 days at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; typically light brown in color, actual color of the roots dependent on substrate composition, water quality, fertilizers, substrate temperature and age of roots.

*Rooting habit*.—Freely branching; medium density.

Plant description:

*Appearance*.—Perennial decorative-type *Chrysanthemum*; stems upright and outwardly spreading giving a uniformly rounded appearance to the plant; plants nearly spherical in overall shape; very freely branching habit, about 20 primary lateral branches develop, each primary lateral branch with multiple secondary branches; pinching enhances lateral branch development; dense and full plant habit.

*Plant height*.—About 30 cm.

*Plant width*.—About 40 cm.

*Lateral branches*.—Length: About 20 cm to 22 cm. Diameter: About 2 mm to 3 mm. Internode length: About 1 cm. Strength: Strong, flexible. Aspect: Upright to outwardly spreading. Texture: Pubescent; longitudinally ridged. Luster: Matte. Color: Close to 145A.

*Leaves*.—Arrangement: Alternate, simple. Length: About 3.5 cm to 4 cm. Width: About 2 cm to 2.5 cm. Apex: Rounded to cuspidate. Base: Attenuate. Margin: Palmately lobed and serrate, sinuses between lateral lobes divergent to parallel. Texture, upper and lower surfaces: Slightly pubescent. Luster, upper and lower surfaces: Matte. Color: Developing leaves, upper surface: Close to 145A. Developing leaves, lower surface: Close to 145B. Fully expanded leaves, upper surface: Close to 139C; venation, close to 148C. Fully expanded leaves, lower surface: Close to 145B; venation, close to 147B to 147C. Petioles: Length: About 1 cm. Diameter: About 2 mm. Texture, upper and lower surfaces: Slightly pubescent and slightly rough. Luster, upper and lower surfaces: Matte. Color, upper surface: Close to 139C. Color, lower surface: Close to 145B.

Inflorescence description:

*Appearance*.—Decorative-type inflorescence form; inflorescences borne on terminals above foliar plane; disc and ray florets arranged acropetally on a capitulum.

*Fragrance*.—Faintly fragrant.

*Flowering time*.—Under natural season conditions, plants flower in early September in Belgium.

*Postproduction longevity*.—Inflorescences maintain good color and substance for about seven weeks on the plant grown in an outdoor nursery; inflorescences persistent.

*Quantity of inflorescences*.—Freely flowering habit with about 20 inflorescences developing per lateral branch with numerous inflorescences developing per plant.

*Inflorescence buds*.—Height: About 4 mm. Diameter: About 7 mm. Shape: Globular. Texture: Smooth. Color: Close to 145A.

*Inflorescence size and shape*.—Diameter: About 3.5 cm. Depth (height): About 2 cm. Disc diameter: About 1 mm. Shape: Circular; raised dome. Receptacle diameter: About 3 mm. Receptacle height: About 2.5 mm to 3 mm. Receptacle texture: Smooth, glabrous. Receptacle color: Close to 144B.

*Ray floret*.—Quantity and arrangement: About 200 or more ray florets per inflorescence arranged in about ten whorls. Length: About 5 mm to 10 mm. Width: About 3 mm. Shape: Oval. Apex: Rounded. Base: Attenuate. Margin: Entire. Aspect: Mostly flat. Texture, upper and lower surfaces: Smooth, glabrous. Luster, upper and lower surfaces: Matte. Color: When opening and fully opened, upper surface: Close to 15B; color becoming closer to 15D with development. When opening and fully opened, lower surface: Close to 15D, color becoming closer to 18C with development.

*Disc florets*.—Quantity and arrangement: About 20 disc florets per inflorescence and massed at the center of the receptacle; disc florets inconspicuous. Length: About 3 mm. Diameter: About 0.5 mm to 1 mm. Shape: Tubular, elongated; apices acute. Color, immature: Apex: Close to 145A. Mid-section: Close to 145A. Base: Close to 145A. Color, mature: Apex: Close to 12A. Mid-section: Close to 12A. Base: Close to 12A.

*Phyllaries*.—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Luster, upper and lower surfaces: Matte. Color, upper surface: Close to 137A. Color, lower surface: Close to N137B.

*Peduncles*.—Length, terminal peduncle: About 3 cm. Length, fourth peduncle: About 4 cm. Length, seventh peduncle: About 5 cm. Diameter: About 4 mm. Angle: About 30° from vertical. Strength: Moderately strong. Texture: Slightly pubescent. Luster: Matte. Color: Close to 145A.

*Reproductive organs*.—Androecium: None observed. Gynoecium: None observed.

*Seeds and fruit*.—Seed and fruit production have not been observed on plants of the new *Chrysanthemum*.

Disease & pest resistance: Resistance to pathogens and pests common to *Chrysanthemum* plants has not been observed on plants of the new *Chrysanthemum* grown under commercial production conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Akilon Gold' as illustrated and described.

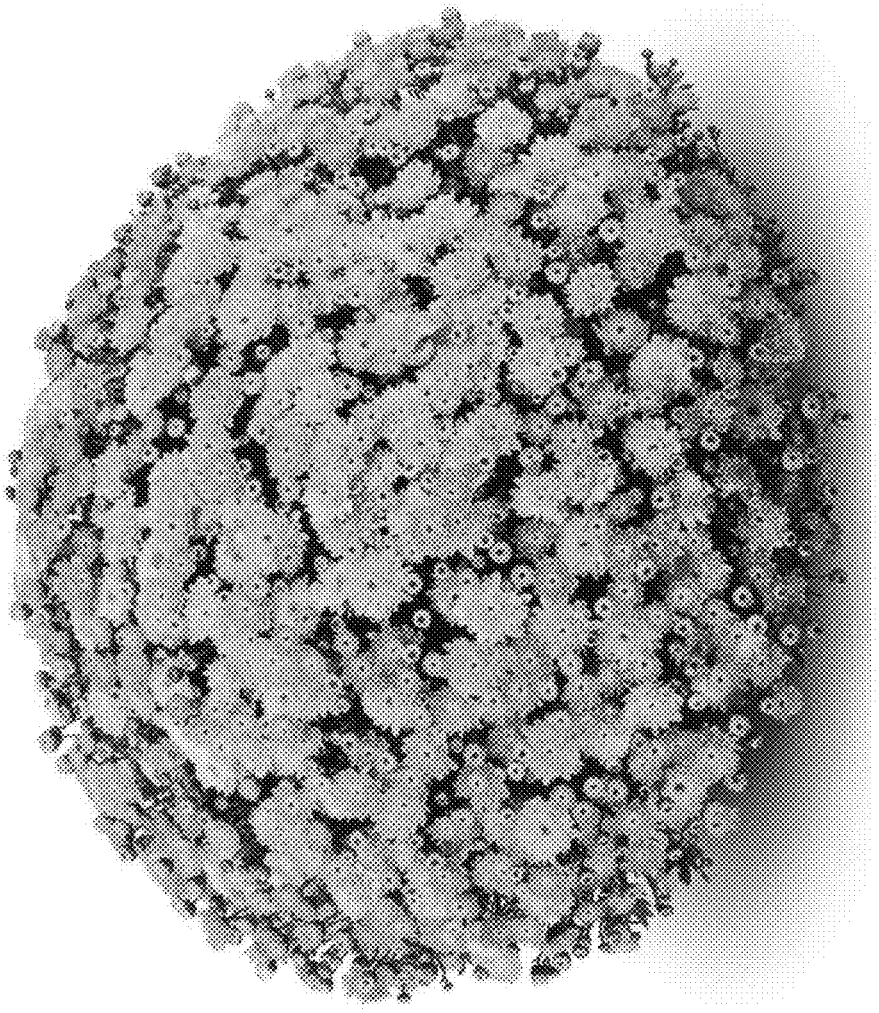

* * * * *